(12) United States Patent
Sumner, Jr. et al.

(10) Patent No.: US 6,380,352 B1
(45) Date of Patent: Apr. 30, 2002

(54) POLYESTER PRECURSOR PURIFICATION PROCESS

(75) Inventors: Charles Edwan Sumner, Jr.; Ronald Buford Sheppard, both of Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/812,581

(22) Filed: Mar. 20, 2001

Related U.S. Application Data

(60) Provisional application No. 60/228,695, filed on Aug. 29, 2000.

(51) Int. Cl.$^7$ .................................................. C08F 6/00
(52) U.S. Cl. ........................ 528/480; 528/271; 528/272
(58) Field of Search ................................ 528/271, 272, 528/480

(56) References Cited

U.S. PATENT DOCUMENTS

| | | |
|---|---|---|
| 3,487,100 A | 12/1969 | Arai et al. |
| 3,501,420 A | 3/1970 | Stevenson |
| 5,597,891 A | 1/1997 | Nelson et al. |
| 5,648,032 A | 7/1997 | Nelson et al. |

FOREIGN PATENT DOCUMENTS

| | | |
|---|---|---|
| JP | 50-142537 | 11/1975 |

*Primary Examiner*—Terressa M. Boykin
(74) *Attorney, Agent, or Firm*—Karen A. Harding; J. Frederick Thomsen; Wendell Ray Guffey

(57) ABSTRACT

Disclosed is a process for the purification of a polyester precursor wherein a polyester oligomer derived from terephthalic acid and one or more glycols or diols is purified or decolorized by hydrogenating the oligomer to convert colored impurities to colorless compounds and thereby improve the color of the oligomer. The colored impurities are present in the terephthalic acid used to prepare the oligomers and are formed during the manufacture of terephthalic acid. The purified/decolorized oligomer obtained from the disclosed process may be used to prepare high molecular weight polyesters.

11 Claims, No Drawings

POLYESTER PRECURSOR PURIFICATION PROCESS

RELATED INFORMATION

This application claims the benefit of U.S. Provisional Application Serial No. 60/228,695 filed Aug. 29, 2000 titled "Method for the Production of High Quality PET from Crude Terephthalic Acid".

BACKGROUND OF THE INVENTION

Polyethylene terephthalate (PET) is currently produced by the polycondensation of purified terephthalic acid (PTA) with ethylene glycol. The purchase or manufacture of PTA represents a major cost in raw material for PET manufacture and other PTA containing polyesters and a major portion of the PTA process is devoted to the purification of crude terephthalic acid. Crude terephthalic acid must be purified to be useful for the manufacture of high quality, low color polyesters. Crude terephthalic acid may be purified to produce PTA by the catalytic hydrogenation of colored impurities with simultaneous conversion of 4-carboxybenzaldehyde (CBA) to p-toluic acid and subsequent crystallization of the product (PTA). The purification is carried out by dissolution of CTA in deionized water at 260–280° C. to give a 20 to 30% solution. The resulting solution is treated with hydrogen in the presence of a fixed-bed catalyst (usually Pd/C). The hydrogenated solution is fed to a series of crystallizers where it is carefully cooled to produce crystalline PTA. The resulting PTA is collected by filtration and must be dried before use. Due to the high temperatures involved, the process must be carried out in expensive titanium pressure vessels and is energy intensive. As a result, the purification of CTA to PTA requires a large amount of capital which significantly adds to the cost of PTA. This cost is naturally added to the cost of the final polyester product. Elimination of the capital needed to produce PTA, or the use of CTA in the place of PTA would significantly lower the cost of polyester manufacture.

Several processes that involve hydrogenation of terephthalic acid (TPA) esters to remove color bodies are listed below.

U.S. Pat. No. 3,501,420 discloses the depolymerization of waste PET in an alcohol to give a solution of terephthalic acid esters. The resulting solution is hydrogenated to remove color bodies. In this process, PET is converted to mostly monomeric esters before contact with hydrogen. The decolorized solution of TPA esters can be used to prepare high-quality PET. A related patent not specifically intended to produce high quality PET (unexamined Japanese patent application 50-142537) teaches a process to make cyclohexanedimethanol (CHDM) by the depolymerization and hydrogenation of waste PET. In this process, waste PET is depolymerized in ethylene glycol solution in the presence of hydrogen and a hydrogenation catalyst to convert PET into a solution of ethylene glycol esters of cyclohexanedicarboxylic acid. The product of this step is separated from the catalyst and treated again with hydrogen at high pressure in the presence of a second hydrogenation catalyst. The object of the second step is to convert the esters of cyclohexanedicarboxylic acid into a solution of CHDM.

U.S. Pat. No. 3,487,100 discloses that bis-hydroxyethyl terephthalate (BHET) prepared from crude TPA and ethylene glycol can be decolorized by treatment with hydrogen in the presence of a hydrogenation catalyst. The BHET is dissolved in water and filtered to remove oligomeric species (which are insoluble in water). The filtered solution is treated with hydrogen at a temperature range of 50–100° C. Although the hydrogenation treatment reduces fluorenone impurities, the BHET must be in solution and the product must be crystallized from solution before further use. Another disadvantage is that oligomers cannot be processed by this method.

SUMMARY OF THE INVENTION

We have found that colored impurities can be removed from oligomers produced from crude terephthalic acid (CTA) and ethylene glycol by catalytic hydrogenation in the melt-phase over a supported or suspended catalyst. The process provided by the present invention comprises contacting a polyester oligomer or prepolymer comprising terephthalic acid with a supported or suspended hydrogenation catalyst in the presence of hydrogen at a temperature range of about 200 to about 290° C. (The PET oligomer is reported to undergo a spontaneous exotherm at temperatures greater than 330° C.). The molten oligomer mixture is contacted with a supported catalyst in the presence of hydrogen at a temperature range of about 200 to about 280° C. (depending upon the content of ethylene glycol), preferably about 240 to about 270° C., and hydrogen partial pressure of up to about 55.13 bar gauge (barg; 800 pounds per square inch gauge—psig), preferably a hydrogen partial pressure of about 10.34 to 27.57 barg (150 to 400 psig). The resulting hydrogenation product is polymerized by conventional methods to produce high quality polyester. An advantage of the process is the elimination of the need for purified terephthalic acid as a raw material for the manufacture of polyester. This eliminates the processing steps typically found in conventional terephthalic acid purification processes: slurry mixing, slurry dissolving, hydrogenation, crystallization, separation, drying, and yield recovery. The capital required to produce purified oligomers containing terephthalic acid residues is essentially condensed into one low-pressure hydrogenation bed.

The present invention provides a process for the production of high quality polyester, or polyester pre-polymer, using crude terephthalic acid as raw material in place of purified terephthalic acid. The present invention eliminates the need for the expensive equipment required for producing purified terephthalic acid.

DETAILED DESCRIPTION OF THE INVENTION

Crude terephthalic acid (CTA) is the product of the autoxidation of para-xylene prior to hydrogenation. The major impurity found in CTA is 4-carboxybenzaldehyde (CBA). The colored impurities have been identified as a mixture of mainly dicarboxyfluorenone isomers (with lesser amounts of mono- and tri-carboxyfluorenones) and dicarboxybenzil. These highly-colored carboxyfluorenone compounds may be hydrogenated to colorless carboxyfluorene compounds. Other compounds such as dicarboxybenzophenone and dicarboxybiphenyl have been identified in low concentrations. Although essentially any grade of CTA can be used in the preparation of the oligomers employed as the starting material for the process of the present invention, the CTA used typically contains less than about 4000 ppm of CBA, preferably less than 700 ppm CBA, and most preferably from about 50 to 250 ppm CBA.

CTA typically is reacted with at least one diol at a temperature between about 200 and about 280° C. to produce an oligomer which may be hydrogenated in accordance with the present invention. Suitable esterification pressures include, but are not limited to those up to about 27.6 barg (400 psig) and preferably up to about 13.8 barg (200 psig). The reaction can be self-acid catalyzed or catalyzed with a suitable esterification catalyst such as titanium or organic or inorganic acids. The oligomer mixture typically is produced continuously in a series of one or more reactors. Two reactors are frequently used in commercial practice. Alternatively, the monomer and oligomer mixture may be produced in one or more batch reactors. Suitable reactors for esterification are known in the art and need not be described here. The esterification is generally conducted from about 1 to about 4 hours. It should be understood that generally, the lower the reaction temperature, the longer the reaction time. The product of the esterification reaction is an oligomer mixture having a degree of polymerization (DP) of about 2 to about 20 and containing impurities such as CBA and color bodies. The oligomer preferably has a DP of about 2 to 10, most preferably about 3 to 5, wherein DP is defined as the number average molecular weight of the oligomer divided by the molecular weight of the repeat unit. The oligomers which may be employed in the present invention also may be characterized by the general formula:

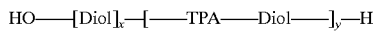

HO——[Diol]$_x$—[——TPA——Diol——]$_y$—H wherein Diol is a divalent residue of a diol or glycol component such as ethylene glycol, 1,4-cyclohexanedimethanol and the like, TPA is the divalent residue of terephthalic acid, x is 0 or 1, and y has an average value of about 2 to 20. The oligomer starting material of our novel process is insoluble in water and thus is distinguished from BHET that is hydrogenated as described in U.S. Pat. No. 3,487,100. The oligomer has a b* value of at least 3, typically in the range of about 4 to 7. The b* values described and reported herein were determined using a L,a,B Color scale b* color measurement measured using ASTM color test on a Hunter Ultra Scan 8000 spectrometer.

The decolorized oligomer mixture may be polymerized by conventional methods used to produce polyesters. The polymerization or polycondensation is conducted in conventional reactors, which are known in the art in continuous or batch modes.

Suitable polycondensation catalysts include compounds of titanium, gallium, germanium, tin, antimony, aluminum, bismuth, silicon, zirconium, compounds of antimony, germanium, titanium or mixtures thereof are preferred. The amount of catalyst added is from about 5 to about 400 ppm and preferably between about 20 to about 300 ppm when germanium or antimony is used. The oligomer mixture undergoes melt-phase polycondensation to produce a precursor polymer which has a degree of polymerization from about 20 to about 120. The precursor polyester is produced in a series of one or more reactors operating at elevated temperatures. To facilitate removal of excess glycols, water, alcohols and other reaction products, the polycondensation reactors are run under a vacuum or purged with an inert gas. Inert gas is any gas that does not cause unwanted reactions or product characteristics. Suitable gases include, but are not limited to $CO_2$, argon, helium, and nitrogen.

The polyester product from the polycondensation reaction is often pelletized for ease of handling. For crystallizable polyesters, the polyester is then crystallized and polymerized further in the solid state, using equipment and conditions which are known in the art. However, crystallizable polyesters of the present invention may also be fed directly to molding equipment without pelletization or solid stating, by processes such as, but not limited to those which are disclosed in U.S. Pat. No. 5,597,891; U.S. Pat. No. 5,648,032, the disclosure of which is incorporated herein by reference.

The hydrogenation-decolorization process of the present invention normally is carried out on the oligomer which is formed in the process of making high molecular weight polyesters. However, it may be possible to utilize the present invention at other points in the polyester manufacturing process so long as the feed material to be hydrogenated is in a liquid form capable of being pumped through the selected hydrogenation reactor and contacting the catalyst to effect the desired reaction. For example, the hydrogenation feed also may be a prepolymer. The hydrogenation step could be conducted as early as the first oligomer-forming reactor when a granular hydrogenation catalyst is used and as early as between the first and second oligomer-forming reactors using a fixed and/or trickle bed reactor. It may be possible to conduct the hydrogenation step between esterification and polycondensation, after polycondensation, or at any point in between. In embodiments wherein the selected polycondensation catalyst reacts with the hydrogenation catalyst it may be preferable to conduct the hydrogenation prior to adding the polycondensation catalyst.

The process of our invention may be carried out by contacting a melt of the terepthalic acid-containing oligomer with hydrogen in the presence of a supported or suspended catalyst at a temperature of about 200 to 280° C. (depending upon the content of ethylene glycol), preferably about 240 to about 270° C., and, in some embodiments, more preferably about 250° C. to about 260° C. and a hydrogen pressure of about 3.45 to 55.13 barg (about 50 to 800 psig). Preferably, the hydrogen pressure is from about 10.34 to 27.57 barg (150 to 400 psig) and more preferably from about 10.34 to 20.68 barg (about 150 to 300 psig). Suitable hydrogenation times include those up to about three hours. It should be appreciated that hydrogenation times will vary with the amount and activity of the catalyst selected as well as the partial pressure of hydrogen and mode of operation. The hydrogenation process may be carried out in a batch, semi-continuous or continuous mode of operation using a slurry or fixed bed of catalyst. The process preferably is carried out in a continuous mode of operation utilizing a trickle bed reactor wherein a melt of the oligomer flows over and through one or more beds of a supported hydrogenation catalyst at elevated temperature and pressure. The hydrogenation may be carried out in the presence of a diluent such as the diol, e.g., ethylene glycol, used in the preparation of the oligomer. The amount of diluent used may be in the range of about 5 to 50 weight percent based on the weight of the oligomer.

Examples of the hydrogenation catalysts which may be used in our novel process include the platinum group metals, such as ruthenium, rhodium, palladium, platinum and osmium. Nickel also may be used. Suitable catalysts are commercially available from Englehard and Sud Chemie. Preferred hydrogenation catalysts include palladium, platinum and nickel catalysts, especially supported catalysts comprising about 0.1 to 10 weight percent palladium or platinum on a catalyst support material. Suitable catalyst support materials include, but are not limited to, $ZrO_2$, carbon, silica, alumina, zeolites, $TiO_2$ and mixtures thereof with carbon being preferred. The oligomer which has been hydrogenated in accordance with the present invention has a b* values of less than about 3, preferably less than about 2, and contains less than 250 ppm CBA.

The polyesters which may be produced from the oligomers decolorized in accordance with the present invention include polyester homopolymers and copolymers that are suitable for use in a wide variety of applications including packaging, film, sheet, coatings, adhesives, molded articles and the like. Food packaging is a particularly preferred use for certain polyesters of the present invention. The polyesters comprise a dicarboxylic acid component comprising terephthalic acid or isophthalic acid, preferably at least about 50 mole % terephthalic acid, and in some embodiments, preferably at least about 75 mole % terephthalic acid and a diol component comprising at least one diol selected from ethylene glycol, cyclohexanedimethanol, diethylene glycol, butanediol and mixtures thereof. The polyesters may further comprise comonomer residues in amounts up to about up to about 50 mole percent of one or more different dicarboxylic acids and or up to about up to about 50 mole percent of one or more diols on a 100 mole % dicarboxylic acid and a 100 mole % diol basis. In certain embodiments comonomer modification of the dicarboxylic acid component, the glycol component or each individually of up to about 25 mole % or up to about 15 mole % may be preferred. Suitable dicarboxylic acid comonomers comprise aromatic dicarboxylic acids, esters of dicarboxylic acids, anhydrides of dicarboxylic esters, and mixtures thereof. More specifically suitable dicarboxylic acid comonomers include aromatic dicarboxylic acids preferably having 8 to 14 carbon atoms, aliphatic dicarboxylic acids preferably having 4 to 12 carbon atoms, or cycloaliphatic dicarboxylic acids preferably having 8 to 12 carbon atoms. Examples of dicarboxylic acid comonomers comprise phthalic acid, isophthalic acid, naphthalene-2,6-dicarboxylic acid, cyclohexanedicarboxylic acid, cyclohexanediacetic acid, diphenyl-4,4'-dicarboxylic acid, dipheny-3,4'-dicarboxylic acid, succinic acid, glutaric acid, adipic acid, azelaic acid, sebacic acid, mixtures thereof and the like.

Suitable diol comonomers comprise cycloaliphatic diols preferably having 6 to 20 carbon atoms or aliphatic diols preferably having 3 to 20 carbon atoms. Examples of such diols comprise triethylene glycol, propane-1,3-diol, butane-1,4-diol, pentane-1,5-diol, hexane-1,6-diol, neopentyl glycol, 3-methylpentanediol-(2,4), 2-methyl-1,4-pentanediol, 2,2,4-trimethylpentane-diol-(1,3), 2-ethylhexanediol-(1,3), 2,2-diethylpro-pane-diol-(1,3), hexanediol-(1,3), 1,4-di-(hydroxyethoxy)-benzene, 2,2-bis-(4-hydroxycyclohexyl)-propane, 2,4-dihydroxy-1,1,3,3-tetramethyl-cyclobutane, 2,2,4,4 tetramethylcyclobutanediol, 2,2-bis-(3-hydroxyethoxyphenyl)-propane, 2,2-bis-(4-hydroxypropoxyphenyl)-propane, isosorbide, hydroquinone, mixtures thereof and the like. Polyesters may be prepared from two or more of the above diols.

Preferred comonomers comprise isophthalic acid, dimethyl isophthalate, dimethyl-2,6-naphthalenedicarboxylate, 2,6-naphtha lenedicarboxylic acid, diethylene glycol, 1,4-cyclohexane-dimethanol, 1,4-butanediol, trimellitic anhydride, mixtures thereof and the like. Bifunctional comonomers, such as hydroxybenzoic acid, also may be included.

The polyesters of the present invention may also contain small amounts of trifunctional or tetrafunctional comonomers such as trimellitic anhydride, trimethylolpropane, pyromellitic dianhydride, pentaerythritol, and other polyester forming polyacids or polyols generally known in the art. Also, although not required, additives normally used in polyesters may be used if desired. Such additives include, but are not limited to colorants, toners, pigments, carbon black, glass fibers, fillers, impact modifiers, antioxidants, stabilizers, flame retardants, reheat aids, acetaldehyde reducing compounds, oxygen scavenging compounds, barrier improving additives, such as platelet particles and the like.

As used in the specification and concluding claims, residue refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —$OCH_2CH_2O$— repeat units in the polyester, regardless of whether ethylene glycol is used to prepare the polyester. Similarly, a sebacic acid residue in a polyester refers to one or more —$CO(CH_2)_8CO$— moieties in the polyester, regardless of whether the residue is obtained by reacting sebacic acid or an ester thereof to obtain the polyester.

Copolymers of isophthalic acid can be produced from crude isophthalic acid without first producing purified isophthalic acid since the colored impurities in the crude isophthalic acid will also be removed by the hydrogenation treatment. Similar processing steps are removed for the isophthalic acid process as described in the terephthalic acid process.

The CBA present in the oligomer feed material is converted into p-toluic acid by the hydrogenation process although a significant amount of the CBA is converted into a polymerizable product, 4-hydroxymethylbenzoic acid, depending on hydrogenation conditions. Thus, it may be preferable to maintain the CBA concentration as low as possible. Colored impurities are usually present in CTA in concentrations of around 100 ppm, and their hydrogenated products are found in PTA in similar (although lesser) amounts. Thus, no new compounds are added to the oligomer product by the process of the present invention.

This invention is further illustrated by the following examples of preferred embodiments thereof, although it will be understood that these examples are included merely for purposes of illustration and are not intended to limit the scope of the invention unless otherwise specifically indicated.

EXAMPLE 1

A 300 mL titanium autoclave equipped with a glass liner was charged with an oligomer (50 g) prepared by the reaction of ethylene glycol and CTA in a 1.3/1 mole ratio respectively at 260° C. for 2 hours. The oligomer had a L,a,B Color scale b* color measurement of 6.9 as measured using ASTM color test on a Hunter Ultra Scan 8000 spectrometer, and a degree of polymerization of 4.5. This oligomer is the starting material for Examples 1–6 listed below. Ethylene glycol (25 g) and 0.5% Pd/C hydrogenation catalyst (1 g) were added and the resulting mixture was pressurized to 1.03 barg (about 15 psig) with hydrogen. The mixture was heated to 214° C. for 90 minutes while the pressure was maintained at 6.34 barg (approximately 92 psig) with hydrogen. After cooling, the mixture was removed from the autoclave and ground into a powder (after removal of large catalyst particles). The color measurement was made on the ground product as described above. The b* of the product was 1.9.

EXAMPLE 2

A 300 mL titanium autoclave equipped with a glass liner was charged with the oligomer (75 g) described in Example 1 and 0.5% Pd/C hydrogenation catalyst (1 g). The resulting mixture was pressurized to 1.03 barg (about 15 psig) with hydrogen. The mixture was heated to 235° C. for 90 minutes while the pressure was maintained at 17.92 barg (260 psig) with hydrogen. After cooling, the mixture was removed from the autoclave and ground into a powder (after removal of large catalyst particles). The color measurement was made on the ground product as described in Example 1. The b* of the product was 1.4.

EXAMPLES 3–5

The procedure of Example 2 was followed except that the temperature and pressure were varied as listed in Table 1. The b* for each polymer was measured as described in Example 1. The results are summarized in Table 1.

TABLE 1

| Example No. | Temperature (° C.) | H$_2$ Pressure (psi) | B* |
|---|---|---|---|
| starting material | | | 6.9 |
| 1 | 214 | 92 | 1.9 |
| 2 | 235 | 260 | 1.4 |
| 3 | 265 | 320 | 2.4 |
| 4 | 238 | 170 | 0.4 |
| 5 | 240 | 130 | 1.4 |

EXAMPLES 7–36

PET oligomer (1.5 kg samples) prepared as described in Example 1 and having a degree of polymerization of 3.9 to 5.8 was hydrogenated in the presence of a 0.5 weight percent palladium-on-carbon catalyst using varying conditions of temperature and pressure and varying amounts of catalyst. The oligomer and catalyst were charged to a 3.8 liter (1 U.S. gallon) titanium autoclave equipped with a bottom flush valve (fitted with a titanium screen) connected to a sampling leg fitted with aluminum heat blocks wrapped with heat tape. The temperature of the heat blocks was monitored by means of a thermocouple inserted into the blocks and was maintained at 260° C. The autoclave was pressurized to 100 psig with hydrogen and heated to the desired temperature. When the temperature reached 160° C. the mixture was stirred at 400 revolutions per minute. When the mixture reached the desired temperature, a sample was taken through the bottom flush valve. The pressure was adjusted to the desired pressure by the addition of hydrogen and the stirring speed was increased to 900 rpm. Samples were taken at 30-minute intervals with the last sample taken after 90 minutes of operation at the predetermined conditions. The samples were saponified with methanol and analyzed by gas chromatography for the methyl esters of CBA, p-toluic acid, 1,4-cyclohexanedicarboxylic acid (CHDA), 2,6- and 2,7-dicarboxyfluorenones, and 2,6- and 2,7-dicarboxyfluorenes. The conditions and amount of catalyst employed in each of the experiments of Example 7–38 and the concentration of colored dicarboxyfluorenones present in the oligomer initially and during the hydrogenation are shown in Table 2 wherein Temp is the temperature of the hydrogenation in ° C., Press is the hydrogen pressure in barg at the temperature given, and Cat is the g of 0.5 weight percent palladium-on-carbon catalyst used. The values given below 0, 30, 60 and 90 refer to mg of dicarboxyfluorenones present in a kg of the oligomer initially (Sampling Time=0), after 30 minutes of hydrogenation (Sampling Time=30 minutes), after 60 minutes of hydrogenation (Sampling Time=60 minutes), and after 90 minutes of hydrogenation (Sampling Time=90 minutes). The values given for CHDA refer to the mg CHDA present in a kg of the oligomer after 90 minutes of hydrogenation.

TABLE 2

| Example No. | Temp | Press | Cat | Dicarboxyfluorenone Concentration | | | | CHDA |
|---|---|---|---|---|---|---|---|---|
| | | | | 0 | 30 | 60 | 90 | |
| 7 | 240 | 13.8 | 11.4 | 135 | 116 | 107 | 97 | 746 |
| 8 | 240 | 27.6 | 11.4 | 138 | 108 | 79 | 77 | 1783 |
| 9 | 240 | 41.4 | 11.4 | 147 | 141 | 106 | 95 | 2259 |
| 10 | 240 | 55.1 | 11.4 | 152 | 112 | 85 | 71 | 3562 |
| 11 | 240 | 55.1 | 11.4 | 138 | 131 | 93 | 63 | 3446 |
| 12 | 240 | 27.6 | 5.7 | 69 | 58 | 66 | 59 | 339 |
| 13 | 240 | 41.4 | 5.7 | 34 | 30 | 25 | 23 | 518 |
| 14 | 260 | 27.6 | 11.4 | 5 | 3 | 2 | 2 | 459 |
| 15 | 260 | 41.4 | 11.4 | 58 | 38 | 27 | 29 | 2023 |
| 16 | 260 | 27.6 | 11.4 | 192 | — | 145 | 102 | 1945 |
| 17 | 260 | 27.6 | 11.4 | 187 | 155 | 143 | 129 | 1014 |
| 18 | 260 | 41.4 | 11.4 | 170 | — | 178 | 122 | 867 |
| 19 | 260 | 13.8 | 11.4 | 179 | — | 147 | 103 | 805 |
| 20 | 260 | 41.4 | 11.4 | 152 | 93 | 71 | 48 | 3048 |
| 21 | 260 | 13.8 | 11.4 | 184 | 142 | 140 | 104 | 231 |
| 22 | 260 | 41.4 | 11.4 | 213 | 165 | 125 | 122 | 1638 |
| 23 | 260 | 27.6 | 5.7 | 272 | 251 | 257 | 253 | 242 |
| 24 | 260 | 41.4 | 5.7 | 262 | 270 | 243 | 233 | 661 |
| 25 | 260 | 13.8 | 5.7 | 154 | 147 | 146 | 136 | 683 |
| 26 | 260 | 27.6 | 5.7 | 186 | 155 | 162 | 140 | 1165 |
| 27 | 260 | 41.4 | 5.7 | 175 | 193 | 185 | 180 | 1657 |
| 28 | 260 | 27.6 | 5.7 | 36 | 38 | 41 | 34 | 608 |
| 29 | 280 | 13.8 | 11.4 | 205 | 113 | 88 | 72 | 923 |
| 30 | 280 | 27.6 | 11.4 | 144 | 104 | 55 | 40 | 2947 |
| 31 | 280 | 41.4 | 11.4 | 157 | 118 | 86 | 81 | 4034 |
| 32 | 280 | 55.1 | 11.4 | 131 | 109 | 70 | 54 | 3897 |
| 33 | 280 | 41.4 | 5.7 | 103 | 94 | 90 | 97 | 832 |
| 34 | 280 | 27.6 | 5.7 | 66 | 71 | 68 | 58 | 293 |
| 35 | 280 | 13.8 | 5.7 | 77 | 77 | 73 | 73 | 156 |
| 36 | 280 | 27.6 | 11.4 | 82 | 54 | 46 | 53 | 791 |

EXAMPLES 37–44

A 40.64 cm (16-inch) piece of 2.54 cm (1-inch) stainless steel tube equipped with a 60 mesh screen over the bottom was charged with 126 mL of a 1% palladium-on-carbon catalyst having an average diameter of 1-mm. The reactor was heated by means of aluminum heat blocks equipped with band heaters. The temperature was monitored by thermocouples inserted into the heat blocks. The temperature of the catalyst bed was monitored by a thermocouple inserted into the catalyst bed. The reactor was connected to an oligomer feed line and a gas feed line at the top, and a collection pot at the bottom. The collection pot was vented at the top to a back-pressure regulator by which the pressure of the reactor and a purge of the reactor gasses were controlled. The collection pot was connected to an in-line sintered metal filter (7 microns), which was connected to a high-temperature metering valve that emptied into a 300 mL glass kettle. The top of the glass kettle was connected to the metering valve and was equipped with a N$_2$ inlet and gas outlet, and was wrapped with heating coils. PET oligomer was melted in 3-neck flask equipped with a mechanical stirrer, condenser, and glass tube on the bottom that was connected to a 6.4 mm (0.25-inch) stainless steel tube. The steel tube was connected to a Braun-Lube positive displacement pump that could pump the molten oligomer to the reactor at a rate of from 1 mL/minute to 12.5 mL/minute. The pump head and the steel tubes (feed lines) were encased in aluminum heat blocks that were heated with either band heaters or cartridge heaters. The H$_2$ feed lines were not heated. Mass flow controllers controlled the flow rate of H2. The H$_2$ flow rate was varied between 15 and 80 mL/minute.

The starting oligomers were prepared as described in Example 1 and had a degree of polymerization of 5.8 and 5.1. The concentration of fluorenones in the oligomer (DP=

5.8) used in Examples 37–40 was 227 mg per kg oligomer and the concentration of fluorenones in the oligomer (DP= 5.1) used in Examples 41–44 was 182 mg per kg oligomer The oligomer was fed to the reactor at a rate of either 3 mL/minute or 6 mL/minute, the hydrogen pressure was 10.34 barg (150 psig), and the temperature within the reactor was 260°. The product was collected after the reactor had reached steady-state and a sample was analyzed as described above. The conditions employed in each of the experiments of Examples 37–44 and the concentration of colored dicarboxyfluorenones and CHDA present in the oligomer initially and after the hydrogenation are shown in Table 3 wherein the feed rate is given in mL/minute, and the values given for the fluorenones and the CHDA refer to mg fluorenones and CHDA per kg of oligomer.

TABLE 3

| Example No. | Feed Rate | Fluorenones | CHDA |
| --- | --- | --- | --- |
| 37 | 3 | 1 | 93 |
| 38 | 3 | 15 | 3071 |
| 39 | 3 | 17 | 2609 |
| 40 | 6 | 15 | 841 |
| 41 | 6 | 42 | 683 |
| 42 | 3 | 2 | 1239 |
| 43 | 6 | 0 | 543 |
| 44 | 3 | 0 | 226 |

EXAMPLE 45

A 300 mL titanium autoclave equipped with a glass liner was charged with an oligomer (100 g; degree of polymerization of 5.8) prepared as described in Example 1 and 2% Pd supported on aluminosilicate hydrogenation catalyst (0.57 g). The resulting mixture was pressurized to 1.03 barg (about 15 psig) with hydrogen. The mixture was heated to 260° C. for 90 minutes while the pressure was maintained at 27.6 barg (400 psig) with hydrogen. After cooling, the mixture was removed from the autoclave and ground into a powder (after removal of catalyst particles) and analyzed as described in the previous examples. The results are summarized in Table 4 (given in mg fluorenones per /kg oligomer).

TABLE 4

| Example No. | Fluorenones | CHDA |
| --- | --- | --- |
| Starting oligomer | 314 | 0 |
| 45 | 30 | 2735 |

The invention has been described in detail with particular reference to preferred embodiments thereof, but it will be understood that variations and modifications can be effected within the spirit and scope of the invention.

We claim:

1. A process comprising contacting a polyester oligomer comprising terephthalic acid with a supported or suspended catalyst in the presence of hydrogen at a temperature range of about 200 to about 290° C.

2. A process for the purification of an oligomer having a degree of polymerization of 2 to 20 derived from terephthalic acid and at least one diol which comprises contacting the oligomer in the melt phase with hydrogen at a temperature of about 200 to 290° C. and a hydrogen pressure of up to about 55.13 bar gauge in the presence of a hydrogenation catalyst.

3. The process of claim 2 wherein the hydrogenation catalyst comprises at least one platinum group metals.

4. The process of claim 1 wherein said catalyst is selected from the group consisting of ruthenium, rhodium, palladium, platinum, osmium, nickel and mixtures thereof.

5. The process of claim 1 wherein said catalyst is selected from the group consisting of palladium, platinum, and mixtures thereof deposited on a catalyst support material.

6. The process of claim 5 wherein the catalyst support material is selected from the group consisting of $ZrO_2$, carbon, silica, alumina, zeolites, $TiO_2$ and mixtures thereof.

7. The process of claim 5 wherein said catalyst support comprises carbon.

8. The process of claim 2 wherein the oligomer has a degree of polymerization of 2 to 10.

9. The process of claim 2 wherein the diol comprises ethylene glycol, cyclohexanedimethanol, butanediol or mixtures thereof.

10. A process for the purification of an oligomer having a degree of polymerization of about 3 to 5 and a b* color value of about 4 to 7 derived from terephthalic acid and at least one diol selected from the group consisting of ethylene glycol, cyclohexanedimethanol, butanediol and mixtures thereof which comprises contacting the oligomer in the melt phase with hydrogen at a temperature of about 240 to 270° C. and a hydrogen pressure of about 10.34 to 27.57 bar gauge in the presence of a hydrogenation catalyst selected from a supported catalyst comprising palladium or platinum deposited upon a catalyst support material.

11. The process of claim 10 wherein the oligomer is derived from terephthalic acid and at ethylene glycol and the catalyst is palladium on carbon catalyst.

* * * * *